(12) United States Patent
Sabatier et al.

(10) Patent No.: US 7,829,666 B2
(45) Date of Patent: Nov. 9, 2010

(54) MAUROTOXIN, PI1 AND HSTX1 DERIVATIVES

(75) Inventors: Jean-Marc Sabatier, Rousset (FR); Kamel Mabrouk, Marseilles (FR); Herve Rochat, Mimet (FR)

(73) Assignee: Cellpep Pharma Inc., Quebec (CA)

( * ) Notice: Subject to any disclaimer, the term of this patent is extended or adjusted under 35 U.S.C. 154(b) by 310 days.

(21) Appl. No.: 12/009,675

(22) Filed: Jan. 22, 2008

(65) Prior Publication Data

US 2009/0062198 A1 Mar. 5, 2009

Related U.S. Application Data

(63) Continuation of application No. 10/363,622, filed as application No. PCT/EP01/10173 on Sep. 3, 2001, now abandoned.

(30) Foreign Application Priority Data

Sep. 4, 2000 (GB) ................................. 0021639.0
Oct. 6, 2000 (GB) ................................. 0024538.1

(51) Int. Cl.
*A61K 38/12* (2006.01)
(52) U.S. Cl. .................................................... 530/317
(58) Field of Classification Search ........................ None
See application file for complete search history.

(56) References Cited

U.S. PATENT DOCUMENTS 5,945,329 A 8/1999 Breddam et al. ............ 435/223

FOREIGN PATENT DOCUMENTS

| WO | PCT/US92/08595 | 10/1991 |
| WO | PCT/US97/08074 | 5/1996 |
| WO | PCT/EP97/07333 | 12/1996 |

OTHER PUBLICATIONS

Blanc E. et al, "Solution Structure of Maurotoxin, a Scorpion Toxin From *Scorpio maurus*, With High Affinity for Voltage-Gated Potassium Channels,". Proteins: Structure, Function, and Genetics 29 (1997); 321-333.*

Blanc E. et al, "Solution Structure of Maurotoxin, a Scorpion Toxin From *Scorpio maurus*, With High Affinity for Voltage-Gated Potassium Channels,". Proteins: Structure, Function, and Genetics 29 (1997) XP-001057482; 321-333.

Carlier E. et al, "Effect of maurotoxin, a four disulfide-bridged toxin from the chactoid scorpion *Scorpio maurus*, on *Shaker* K+ channels,". J. Peptide Res. 55, (2000) XP-000947132; 419-427.

Carlier E. et al, "Disulfide bridge reorganization induced by proline mutations in maurotoxin,". FEBS Letters 489 (2001); 202-207.

Fajloun Z. et al, "Maurotoxin *Versus* Pi1/HsTx1 Scorpion Toxins,". The Journal of Biological Chemistry vol. 275, No. 50 (2000) XP-002198493; 39394-39402.

Fajloun Z. et al, "Synthesis, $^1$H NMR Structure, and Activity of a Three-disulfide-bridged Maurotoxin Analog Designed to Restore the Consensus Motif of Scorpion Toxins,". The Journal of Biological Chemistry vol. 275, No. 18 (2000) XP-002190859; 13605-13612.

Kharrat R. et al, "Maurotoxin, a four disulfide bridge toxin from *Scorpio maurus* venom: purification, structure and action on potassium channels,". FEBS Letters 406 (1997); 284-290.

Lecomte C. et al, "Maurotoxin and the $K_{V1.1}$ channel: voltage-dependent binding upon enantiomerization of the scorpion toxin disulfide bridge $Cys^{31}$-$Cys^{34}$,". J. Peptide Res. 55, (2000) XP-002190858; 246-254.

Olamendi-Portugal T. et al, "A novel structural class of K+-channel blocking toxin from the scorpion *Pandinus imperator*,". Biochem. J. (1996) 315; 977-981.

Sabatier J.-M. et al., "Maurotoxin vs PI1 Scorpion Toxins: Towards New Insights In The Understanding Of Their Distinct Disulfide Bridge Patterns,". p. 216 (2000) XP-001057491; S 152.

Sabatier J.-M. et al., "Synthesis and Characterization of Leiurotoxin I Analogs Lacking One Disulfide Bridge: Evidence That Disulfide Pairing 3-21 Is Not Required for Full Toxin Activity,". Biochemistry (1996) 35 XP-002064839; 10641-10647.

Savarin P. et al., "Structural and functional consequenses of the presence of a fourth disulfide bridge in the scorpion short toxins: solution of the potassium channel inhibitor HsTX1,". Protein Science (1999); 2672-2685.

Tytgat J. et al., "A unified nomenclature for short-chain peptides isolated from scorpion venoms: α-KTx molecular subfamilies,". Nov. 1999 vol. 20.

Zhukov I. et al., "Conservative mutation Met8 → Leu affects the folding process and structural stability of squash trypsin inhibitor CMTI-I,". Protein Science (2000); 273-279.

* cited by examiner

*Primary Examiner*—Cecilia Tsang
*Assistant Examiner*—Thomas S Heard
(74) *Attorney, Agent, or Firm*—Clark & Elbing LLP

(57) ABSTRACT

Derivatives of Maurotoxin (MTX) in which the native disulfide bridge pattern (Cys3-Cys24, Cys9-Cys29, Cys19, Cys31-Cys34) has been disrupted are useful for the treatment of pathologies associated with dysfunctioning and/or activation of $Ca^{2+}$-activated and/or voltage-gated K+ channel subtypes, such as IKCa1 or Kv1.2. In one group of derivatives, one or two of the amino acid residues of maurotoxin have been replaced by different amino acid residues resulting in the disulfide bridge pattern being changed to Cys3-Cys24, Cys9-Cys29, Cys13-Cys31, Cys19-Cys34. Exemplary substitutions include the Arg residue at position 14 and/or the Lys residue at position 15 replaced by a Gln residue and the Gly residue at position 33 replaced by an Ala residue. Pi1 and HsTx1 derivatives with disrupted native disulfide bridge patterns are similarly useful.

14 Claims, No Drawings

SEQUENCE LISTING

```
<160> NUMBER OF SEQ ID NOS: 8

<210> SEQ ID NO 1
<211> LENGTH: 34
<212> TYPE: PRT
<213> ORGANISM: Scorpio Maurus palmatus

<400> SEQUENCE: 1

Val Ser Cys Thr Gly Ser Lys Asp Cys Tyr Ala Pro Cys Arg Lys Gln
1               5                   10                  15

Thr Gly Cys Pro Asn Ala Lys Cys Ile Asn Lys Ser Cys Lys Cys Tyr
            20                  25                  30

Gly Cys

<210> SEQ ID NO 2
<211> LENGTH: 35
<212> TYPE: PRT
<213> ORGANISM: Scorpio Pandinus imperator

<400> SEQUENCE: 2

Leu Val Lys Cys Arg Gly Thr Ser Asp Cys Gly Arg Pro Cys Gln Gln
1               5                   10                  15

Gln Thr Gly Cys Pro Asn Ser Lys Cys Ile Asn Arg Met Cys Lys Cys
            20                  25                  30

Tyr Gly Cys
        35

<210> SEQ ID NO 3
<211> LENGTH: 34
<212> TYPE: PRT
<213> ORGANISM: Scorpio Heterometrus spinnifer

<400> SEQUENCE: 3

Ala Ser Cys Arg Thr Pro Lys Asp Cys Ala Asp Pro Cys Arg Lys Glu
1               5                   10                  15

Thr Gly Cys Pro Tyr Gly Lys Cys Met Asn Arg Lys Cys Lys Cys Asn
            20                  25                  30

Arg Cys
```

<210> SEQ ID NO 4
<211> LENGTH: 34
<212> TYPE: PRT
<213> ORGANISM: Artificial Sequence
<220> FEATURE:
<223> OTHER INFORMATION: MTX with Ala in place of Gly at position 33

<400> SEQUENCE: 4

Val Ser Cys Thr Gly Ser Lys Asp Cys Tyr Ala Pro Cys Arg Lys Gln
1               5                   10                  15

Thr Gly Cys Pro Asn Ala Lys Cys Ile Asn Lys Ser Cys Lys Cys Tyr
            20                  25                  30

Ala Cys

<210> SEQ ID NO 5
<211> LENGTH: 34
<212> TYPE: PRT
<213> ORGANISM: Artificial Sequence
<220> FEATURE:
<223> OTHER INFORMATION: MTX with Gln in place of Arg at position 14

<400> SEQUENCE: 5

Val Ser Cys Thr Gly Ser Lys Asp Cys Tyr Ala Pro Cys Gln Lys Gln
1               5                   10                  15

Thr Gly Cys Pro Asn Ala Lys Cys Ile Asn Lys Ser Cys Lys Cys Tyr
            20                  25                  30

Gly Cys

<210> SEQ ID NO 6
<211> LENGTH: 34
<212> TYPE: PRT
<213> ORGANISM: Artificial Sequence
<220> FEATURE:
<223> OTHER INFORMATION: MTX with Gln in place of Lys at position 15

<400> SEQUENCE: 6

Val Ser Cys Thr Gly Ser Lys Asp Cys Tyr Ala Pro Cys Arg Gln Gln
1               5                   10                  15

Thr Gly Cys Pro Asn Ala Lys Cys Ile Asn Lys Ser Cys Lys Cys Tyr
            20                  25                  30

Gly Cys

<210> SEQ ID NO 7
<211> LENGTH: 34
<212> TYPE: PRT
<213> ORGANISM: Artificial Sequence
<220> FEATURE:
<223> OTHER INFORMATION: MTX with Gln-Gln in place of Arg-Lys at
      positions 14-15

<400> SEQUENCE: 7

Val Ser Cys Thr Gly Ser Lys Asp Cys Tyr Ala Pro Cys Gln Gln Gln
1               5                   10                  15

Thr Gly Cys Pro Asn Ala Lys Cys Ile Asn Lys Ser Cys Lys Cys Tyr
            20                  25                  30

Gly Cys

<210> SEQ ID NO 8
<211> LENGTH: 34
<212> TYPE: PRT
<213> ORGANISM: Artificial Sequence

```
-continued

<220> FEATURE:
<223> OTHER INFORMATION: MTX with alpha-amino butyrate (Abu) in place of
      Cys at positions 9, 19, 29 and 34
<220> FEATURE:
<221> NAME/KEY: misc_feature
<222> LOCATION: (9)..(9)
<223> OTHER INFORMATION: Xaa is alpha-amino butyrate (Abu)
<220> FEATURE:
<221> NAME/KEY: misc_feature
<222> LOCATION: (19)..(19)
<223> OTHER INFORMATION: Xaa is alpha-amino butyrate (Abu)
<220> FEATURE:
<221> NAME/KEY: misc_feature
<222> LOCATION: (29)..(29)
<223> OTHER INFORMATION: Xaa is alpha-amino butyrate (Abu)
<220> FEATURE:
<221> NAME/KEY: misc_feature
<222> LOCATION: (34)..(34)
<223> OTHER INFORMATION: Xaa is alpha-amino butyrate (Abu)

<400> SEQUENCE: 8

Val Ser Cys Thr Gly Ser Lys Asp Xaa Tyr Ala Pro Cys Arg Lys Gln
1               5                   10                  15

Thr Gly Xaa Pro Asn Ala Lys Cys Ile Asn Lys Ser Xaa Lys Cys Tyr
            20                  25                  30

Gly Xaa
```

US 7,829,666 B2

MAUROTOXIN, PI1 AND HSTX1 DERIVATIVES

RELATED APPLICATION

This application is a continuation of U.S. patent application Ser. No. 10/363,622 filed Jul. 14, 2003, titled "Maurotoxin, PI1 and HSTX1 Derivatives", which is the U.S. National Phase of PCT International Application No. PCT/EP01/10173, filed Sep. 3, 2001 which claims the benefit of GB Application No. 0021639.0, filed Sep. 4, 2000 and GB Application No. 0024538.1, filed Oct. 6, 2000.

BACKGROUND

The invention relates to derivatives of maurotoxin and of particular toxins belonging to the same structural class of $K^+$ channel-acting short-chain scorpion toxins (less than 40 amino acid residues) that are cross-linked by four disulfide bridges, such as Pi1 and HsTx1.

SUMMARY

Among the toxin derivatives contemplated by the invention are truncated, modified, and mutated toxins (with either natural or non-natural amino acid residues, or non-natural peptide bonds or linkages) with four, or less than four, disulfide bridges. Mimetics of these compounds are also included. The invention also relates to the use of all these derivatives and mimetics for the treatment of neurological disorders, including immunological neurological disorders, associated with their action on modulation or blockade of specific $K^+$ channels, $Ca^{2+}$-activated and/or voltage-gated subtypes, and to pharmaceutical compositions containing them.

DESCRIPTION

Maurotoxin (MTX), a toxin from the venom of the Tunisian chactidae scorpion *Scorpio maurus palmatus*, is a 34-mer peptide cross-linked by four disulfide bridges. The sequence of amino acid residues in MTX is VSCTGSKD-CYAPCRKQTGCPNAKCINKSCKCYGC-NH.sub.2 [SEQ. ID NO. 1]. MTX belongs to a distinct family of short-chain scorpion toxins with less than 40 residues, that are active onto several potassium channel subtypes (Kv and KCa channels). Contrary to most short-chain $K^+$ channel-acting scorpion toxins, this family can be distinguished by the presence of an additional disulfide bridge (four instead of the three commonly present in such toxins). This structural class also includes Pi1 [SEQ. ID NO. 2] and HsTx1 [SEQ. ID NO. 3] from the venoms of the scorpions *Pandinus imperator* and *Heterometrus spinnifer*, respectively. These toxins share from 53 to 68% sequence identity with MTX but display different pharmacological selectivities. For instance, MTX and Pi1 are both active on some $Ca^{2+}$-activated $K^+$ channels, e.g. apamin-sensitive SK channels, whereas HsTx1 is reportedly inactive on these channel types. Also, MTX was found to be active on rat Kv1.3 channels contrary to synthetic Pi1. Interestingly, MTX structurally differs from Pi1 and HsTx1, but also from other "classical" three disulfide-bridged scorpion toxins, by its unique disulfide bridge pattern. In three disulfide-bridged toxins, the half-cystine pairings are of the type C1-C4, C2-C5 and C3-C6 (e.g. charybdotoxin, PO.sub.5, agitoxin 2, leiurotoxin 1). In short-chain four disulfide-bridged toxins, this pattern is altered by the insertion of two additional half-cystines within the amino acid sequence, one located after C3 and the other after C6. As a result, two novel patterns of the disulfide bridges are experimentally found depending on the toxin: (i) a pattern of the type C1-C5, C2-C6, C3-C7 and C4-C8 in both Pi1 and HsTx1 (which corresponds to an organization similar to that observed in three disulfide-bridged toxins), and (ii) an uncommon pattern of the type C1-C5, C2-C6, C3-C4 and C7-C8 in MTX. These two patterns possess in common the first two disulfide bridges but are differing by the two remaining disulfides. Though differences in pharmacological properties between short-chain four disulfide-bridged toxins obviously rely on their distinct amino acid sequences, it is also possible that changes in half-cystine pairings may contribute to either dramatic or discrete conformational alterations and repositioning of key residues that are involved in toxin selectivity. At the pharmacological level, MTX displays an uncommon enlarged specificity, being active—in the picomolar or nanomolar concentration range—on both $Ca^{2+}$-activated $K^+$ channels, e.g. small conductance apamin-sensitive $Ca^{2+}$-activated $K^+$ (SK) channels, and several voltage-gated (Kv) $K^+$ channel subtypes, including Kv1.2.

In J. Biol. Chem., Vol. 275, No. 18, pp 13605-13612, 2000, Fajloun et al have described an MTX derivative with three instead of four disulfide bridges, formed by substituting α-aminobutyrate (Abu) residues for the Cys residues located at positions 19 and 34 (corresponding by numbers to positions C4 and C8). This derivative adopts the α/β scaffold with now conventional half-cystine pairings connecting C1-C5, C2-C6 and C3-C7 but remains lethal in mice by intracerebroventricular injection (LD.sub.50:0.25 .mu.g/mouse).

The invention provides MTX, Pi1 and HsTx1 derivatives, in which specific residue replacements, or a reorganization of half-cystine pairings has taken place, resulting in a novel, highly potent and more selective pharmacological profile.

In one preferred derivative, the substitution of the MTX half-cystine residues (by amino butyrate derivatives) located at positions 9, 19, 29, and 34 (corresponding by numbers to C2, C4, C6, and C8) results in a two disulfide-bridged MTX analog, i.e. VSCTGSKDAbuYAPCRKQTGAbuP-NAKCINKSAbuKCYGAbu-NH.sub.2 [SEQ. ID NO. 8], with novel, non-native arrangement of the half-cystine pairings (Cys3-Cys24 and Cys13-Cys31). Pharmacological assays of this structural analog, [Abu9, 19, 29, 34]-MTX, reveal that the blocking activity is potent (IC50=42 nM) and highly selective for mammalian voltage-gated Kv1.2 channel subtype, although it remains active on $Ca^{2+}$-activated $K^+$ channels.

An alternative approach to replacement of Cys residues with Abu is the replacement of one or two amino acid residues in natural MTX with other residues which prevent the folding of the molecule in such a way that the unconventional C1-C5, C2-C6, C3-C7 and C4-C8 disulfide bridge arrangement can occur. For instance, if neither of the residues at positions 32 and 33 is a Gly or Pro residue, the folding is altered in such a way that the MTX derivative adopts the conventional C1-C5, C2-C6, C3-C7 and C4-C8 of Pi1 and HsTx1. In particular, replacement of the Gly residue at position 33 by an Ala residue substitution, forming [A33]-MTX [SEQ. ID NO. 4], is effective. Substitution of Arg14 and/or Lys15 by Gln to give [Q14]-MTX [SEQ. ID NO. 5], [Q15]-MTX [SEQ. ID NO. 6] or [Q14,Q15]-MTX [SEQ. ID NO. 7] also induces half-cystine pairings between Cys3-Cys24, Cys9-Cys29, Cys13-Cys31 and Cys19-Cys34. [Q15]-MTX in particular was 1,000 times more potent than [Abu9, 19, 29, 34]-MTX on mammalian voltage-gated Kv1.2 (IC50=47 pM).

Contrary to natural MTX and Pi1 which are lethal in C57/BL6 mice (LD50=4 mcg/kg of MTX or 10 mcg/kg of Pi1), MTX and Pi1 derivatives such as [Abu9, 19, 29, 34]-MTX or

[Q15]-MTX are neither lethal nor toxic when injected intracerebroventricularly in these mice at active concentrations (up to 1.25 mg/kg in the case of [Abu9, 19, 29, 34]-MTX). The MTX derivatives, as well as the MTX structurally homologous Pi1 or HsTx1 derivatives, of the invention are thus of potential therapeutic value for treating mammalian (including human) pathologies that are associated with a dysfunctioning of $Ca^{2+}$-activated and/or voltage-gated Kv channel subtypes. Such pathologies include immune and/or neurological diseases like multiple sclerosis, Parkinson's and Alzheimer's diseases, both thought to be associated with a dysfunctioning of $Ca^{2+}$-activated and/or voltage-gated $K^+$ channel subtype(s). The axonal impulse propagation ensures a continued transmission of nervous signals to remote targets. In a number of neuropathies, the nervous conduction is either slowed down or locked. This could be linked to alteration or functional changes of myelinated fibres (demyelinisation or alteration of the membrane properties at the Ranvier nodes). Among these neuropathies are multiple sclerosis (central nervous system; CNS) and Guillain-Barr syndrome (peripheral nervous system). It is now well-admitted that alteration of the axonal function is related to the presence of voltage-gated (Kv) $K^+$ channels (there is a widespread distribution of Kv1.1 and Kv1.2 channel subtypes in nerve terminals throughout the brain, whereas Kv channels—independent of their subtypes—are considered to be ubiquitous, including in the peripheral nervous system), and possibly $Ca^{2+}$-activated $K^+$ channels. In the previously cited neuropathies, $Ca^{2+}$-activated $K^+$ channels and Kv channels are either abnormally exposed in demyelinated or inflammatory lesions, or overexpressed. Therefore, selective $K^+$-channel blockers, including $Ca^{2+}$-activated $K^+$ channel-acting and/or Kv-acting MTX/Pi1/HsTx1-derived peptides such as [Q15]-MTX, Pi1 amidated at C-terminus, [Abu9, 19, 29, 34]-MIX, are of potential therapeutic value as symptomatic therapy of multiple sclerosis and related neuropathies, as well as for use as selective immuno-suppressant drugs by their blocking action on $Ca^{2+}$-activated and/or Kv channels. Further, it can be speculated that such peptide blockers, in the CNS, could enhance transmitter release in pathways affected by progressive neurodegenerative diseases such as Alzheimer's disease.

What is claimed is:

1. An isolated non-native maurotoxin peptide comprising the amino acid sequence of SEQ ID NO: 1 and further comprising an amino acid substitution of the arginine residue at position 14, the lysine residue at position 15, or the glycine residue at position 33, said peptide comprising a disulfide bridge pattern of Cys3-Cys24, Cys9-Cys29, Cys13-Cys31, and Cys19-Cys34.

2. The peptide of claim 1, wherein the amino acid substitution comprises a replacement of the arginine at position 14 with a glutamine residue (SEQ ID NO: 5).

3. The peptide of claim 1, wherein the amino acid substitution comprises a replacement of the lysine at position 15 with a glutamine residue (SEQ ID NO: 6).

4. The peptide of claim 1, wherein the amino acid substitution comprises a replacement of the arginine residue at position 14 and the lysine residue at position 15 with glutamine residues (SEQ ID NO: 7).

5. The peptide of claim 1, wherein the amino acid substitution comprises a replacement of the glycine residue at position 33 with an alanine residue (SEQ ID NO: 4).

6. A pharmaceutical composition comprising an isolated maurotoxin peptide of claim 1 in admixture with a pharmaceutically acceptable diluent or carrier.

7. A pharmaceutical composition comprising an isolated maurotoxin peptide of claim 2 in admixture with a pharmaceutically acceptable diluent or carrier.

8. A pharmaceutical composition comprising an isolated maurotoxin peptide of claim 3 in admixture with a pharmaceutically acceptable diluent or carrier.

9. A pharmaceutical composition comprising an isolated maurotoxin peptide of claim 4 in admixture with a pharmaceutically acceptable diluent or carrier.

10. A pharmaceutical composition comprising an isolated maurotoxin peptide of claim 5 in admixture with a pharmaceutically acceptable diluent or carrier.

11. A method of modulating a $K^+$ channel in a cell, said method comprising contacting said cell with a maurotoxin peptide of claim 1.

12. The method of claim 11, wherein said $K^+$ channel is a $Ca^{2+}$-activated or voltage-gated $K^+$ channel subtype.

13. The method of claim 12, wherein said $Ca^{2+}$-activated or voltage-gated $K^+$ channel subtype is IKCa1 or Kv1.2.

14. The method of claim 11, wherein said maurotoxin peptide blocks said $K^+$ channel.

* * * * *